United States Patent
Mock et al.

(10) Patent No.: US 8,906,029 B2
(45) Date of Patent: Dec. 9, 2014

(54) DEVICE AND METHOD FOR DISPENSING A MATERIAL WITH THERMOPLASTIC PROPERTIES IN A FLOWABLE STATE AT AN OPERATION SITE IN A HUMAN OR ANIMAL PATIENT

(75) Inventors: Elmar Mock, Colombier (CH); Urs Weber, Evilard (CH); Jörg Mayer, Niederlenz (CH)

(73) Assignee: Woodwelding AG, Stansstad (CH)

( * ) Notice: Subject to any disclaimer, the term of this patent is extended or adjusted under 35 U.S.C. 154(b) by 389 days.

(21) Appl. No.: 13/266,903

(22) PCT Filed: May 5, 2010

(86) PCT No.: PCT/CH2010/000116
§ 371 (c)(1),
(2), (4) Date: Jan. 31, 2012

(87) PCT Pub. No.: WO2010/127462
PCT Pub. Date: Nov. 11, 2010

(65) Prior Publication Data
US 2012/0123467 A1    May 17, 2012

Related U.S. Application Data

(60) Provisional application No. 61/175,947, filed on May 6, 2009.

(51) Int. Cl.
| | | |
|---|---|---|
| *A61B 17/58* | (2006.01) | |
| *A61F 2/46* | (2006.01) | |
| *A61B 17/88* | (2006.01) | |
| *A61B 17/04* | (2006.01) | |
| *A61B 17/00* | (2006.01) | |
| *A61F 2/30* | (2006.01) | |

(52) U.S. Cl.
CPC .............. *A61B 17/8836* (2013.01); *A61F 2/46* (2013.01); *A61F 2210/0071* (2013.01); *A61B 2017/0409* (2013.01); *A61B 17/0057* (2013.01); *A61B 2017/00955* (2013.01); *A61F 2002/465* (2013.01); *A61F 2002/30065* (2013.01); *A61B 17/00491* (2013.01); *A61B 17/0401* (2013.01)

USPC .................................. 606/93; 606/92; 606/94

(58) Field of Classification Search
CPC ........... A61B 17/8802; A61B 17/8805; A61B 17/8836
USPC ............ 606/92–94; 433/9, 24, 80, 81, 83, 89, 433/217.1, 219, 226–228.1
See application file for complete search history.

(56) References Cited

U.S. PATENT DOCUMENTS

| | | | | |
|---|---|---|---|---|
| 5,203,697 | A  * | 4/1993 | Malmin | 433/81 |
| 6,558,059 | B1 * | 5/2003 | Hillinger et al. | 401/2 |

(Continued)

FOREIGN PATENT DOCUMENTS

| | | |
|---|---|---|
| EP | 1917924 | 5/2008 |
| EP | 1982662 | 10/2008 |

(Continued)

*Primary Examiner* — Nicholas Woodall
(74) *Attorney, Agent, or Firm* — Rankin, Hill & Clark LLP (57) ABSTRACT

For dispensing a material with thermoplastic properties in a flowable state at an operation site in a human or animal patient, a device is used, which includes the material having thermoplastic properties in a solid state and is equipped for bringing the material into a flowable state at a distal device end positioned at the site where dispensing is desired and for driving the flowable material from this distal device end. The device comprises a rotation drive, a consumable element and a dispenser element, wherein one of the two elements is coupled to the rotation drive and wherein the consumable element comprises the material to be dispensed. The two elements are arranged with parallel longitudinal axes and the dispenser element comprises a distal end piece with a proximal face against which a distal face of the consumable element is held and advanced during dispensing.

15 Claims, 3 Drawing Sheets

(56) References Cited

U.S. PATENT DOCUMENTS

| | | |
|---|---|---|
| 6,981,868 B2 * | 1/2006 | Okawa et al. ............... 433/81 |
| 8,403,664 B2 * | 3/2013 | Jung et al. ................. 433/32 |
| 2008/0167658 A1 | 7/2008 | Kerr et al. |
| 2009/0220909 A1 * | 9/2009 | Muller et al. ............... 433/81 |
| 2010/0049179 A1 | 2/2010 | Kanaoka et al. |
| 2010/0109179 A1 * | 5/2010 | Jensen ....................... 264/16 |
| 2010/0211058 A1 * | 8/2010 | Winterbottom et al. ........ 606/29 |
| 2012/0239049 A1 | 9/2012 | Truckai et al. |

FOREIGN PATENT DOCUMENTS

| | | |
|---|---|---|
| WO | 02/069817 | 9/2002 |
| WO | 2008/095327 | 8/2008 |
| WO | 2009/010247 | 1/2009 |

* cited by examiner

DEVICE AND METHOD FOR DISPENSING A MATERIAL WITH THERMOPLASTIC PROPERTIES IN A FLOWABLE STATE AT AN OPERATION SITE IN A HUMAN OR ANIMAL PATIENT

BACKGROUND OF THE INVENTION

1. Field of the Invention

The invention resides in the field of medical technology and concerns a device and a method for dispensing a material in a human or animal patient. Device and method serve for dispensing a material with thermoplastic properties in a flowable state, i.e. for bringing the material with thermoplastic properties from a solid state into a flowable state and depositing the material in the flowable state at a desired site to re-solidify. Device and method are specifically adapted for dispensing relatively small amounts of the material at an operation site in a human or animal patient but may of course also be used for dispensing the material at any other site. The device, preferably being a hand-held device, either contains the material with thermoplastic properties or is chargeable with it. The material is made flowable in a distal end portion of the device, while this distal end portion is positioned at the site where dispensing is desired.

2. Description of Related Art

Surgical processes in which materials with thermoplastic properties are liquefied in situ, are known e.g. from the publications U.S. Pat. No. 7,335,205, U.S. Pat. No. 7,008,226, WO-2005/079696, or WO-2008/034277. These publications disclose in particular methods for anchoring an implant in tissue with the aid of a material, which has thermoplastic properties and is comprised by the implant, and with the aid of vibration energy, in particular ultrasonic vibration energy. Therein the implant or part thereof is pressed against the tissue or against another implant part whereby the thermoplastic material constituting a surface of the implant or implant part is liquefied and made to penetrate the tissue where, on re-solidification, it constitutes a positive fit connection between the tissue and a portion of the thermoplastic material which was not liquefied.

The publication U.S. Pat. No. 6,620,185 discloses a device for anchoring a suture in an opening in bone tissue, wherein a material with thermoplastic properties is brought into the opening in a flowable state. The material with thermoplastic properties is stored in the dispensing device in a solid state (pellets or flexible rod to be handled like the suture), is driven to a distal device end through a cannula by pressurized air and for being dispensed is melted at this distal end, which for the melting process comprises an electric heating element, or means for inductive heating or heating with ultrasound or laser light.

BRIEF SUMMARY OF THE INVENTION

It is the object of the invention to create a further device and method for dispensing a material with thermoplastic properties in a flowable state at an operation site in a human or animal patient, wherein the device and therewith the method according to the invention is to be simpler and more generally applicable than the above shortly described known device which serves the same purpose.

This object is achieved by device and method as defined in the claims.

According to an aspect of the invention, the material with thermoplastic properties is brought into the flowable state at the distal end of the device (liquefaction site) by heating a distal end of a consumable element comprising the material, wherein the named heating is effected by holding a distal face of the consumable element against a distal portion of a dispenser element and creating a relative rotational movement and therewith friction energy between the consumable element and the dispenser element. Due to this friction energy, the material of the distal end face of the consumable element becomes flowable and, due to the holding against, the flowable material flows from the interface between consumable element and dispenser element to be dispensed and the consumable element is advanced towards the interface for compensating for the dispensed material. Therein at least the force necessary for the named holding against and advancement (advancement force) and possibly the torque for effecting the rotational movement is applied to the proximal end of the consumable element. When a desired amount of the material with thermoplastic properties is dispensed, a rest of the consumable element is separated from the dispensed material by simply distancing the distal end of the device from a site where the dispensing was effected and therewith separating the dispensed part of the material with thermoplastic properties from the rest of the consumable element which remains in the device. The device according to this aspect of the invention comprises a rotation drive arranged in a proximal device region (e.g. in a housing designed for being hand held by an operator) and the dispenser element extends from the proximal device region to a distal device end. The dispenser element comprises a shaft portion and a distal end portion, wherein the end portion has a larger cross sectional area than the shaft portion and therewith a proximal face. The end portion partly closes an axially extending through opening of the shaft portion or protrudes axially from the shaft portion. The consumable element consists at least in a distal section of the material to be dispensed. The consumable element is substantially cylindrical (circular or non-circular cylinder, full or cannulated) and is arranged or arrangeable in a through opening of the shaft portion, around the shaft portion or possibly beside the shaft portion, and its distal face is in contact with the proximal face of the end portion. Either the dispenser element or the consumable element is coupled to the rotation drive for rotation around its longitudinal axis and the consumable part is held against the proximal face of the end portion by an advancement force. The advancement force is applied to the consumable element directly or indirectly by an operator or by a resilient element arranged to resiliently close a load frame in which the consumable element is put under a compressive load and the shaft portion of the dispenser element is put under a tensile load. The advancement force is transmitted through the consumable element along its full axial length.

In a variant, the liquefaction site is chosen to be at the proximal end of the consumable element. In this variant, the proximal face of the consumable element is in contact with a distal face of the end portion of the dispenser element, while the dispenser element and the consumable element are subject to a relative rotational movement. In this variant, the advancement force presses the dispenser element in the distal direction, and counter element is used to couple a counter force into the consumable element, the counter element comprising a distal end portion that has a larger cross sectional area than a shaft portion and therewith a proximal face that couples the counter force into the consumable element.

More in general, therefore, the device for dispensing a material with thermoplastic properties in a flowable state at an operation site in a human or animal patient comprises, in addition to the rotation drive, a dispenser element comprising a shaft portion with a longitudinal axis extending from a proximal end of the shaft portion to a distal end portion which is arranged at a distal end of the shaft portion and comprises a proximal or distal face. The distal end portion may have a larger cross sectional area than the shaft portion, but for the variant with the proximal liquefaction site this is not a requirement. The device further comprises a consumable element with a longitudinal axis extending from a proximal end to a distal end, at least a (distal or proximal) portion of the consumable element consisting of the material with thermoplastic properties. Either the consumable element (for example a proximal end thereof) or a proximal end of the shaft portion is adapted to the rotation drive to be coupled thereto and the consumable element or the shaft portion is designed to be capable of transmitting the torque of the rotation drive to its distal end, and the other one of the consumable or dispenser element is adapted to be held for not rotating. The consumable element and the dispenser element are arranged or arrangeable with their longitudinal axes parallel to each other, and with a distal or proximal face of the consumable element in contact with the proximal or distal face of the end portion and the two faces are capable of being pressed against each other with an advancement force putting a compressive load on the consumable element along its longitudinal axis and being applied to the proximal end of the consumable element and a counter force to the distal end of the consumable element. In many configurations, the embodiments with the liquefaction site being at the distal end of the device are preferred. One reason is that this makes possible that the material is dispensed as deeply in the tissue as possible, and (in case the tissue opening has to be made by the surgeon) it is not necessary to make a tissue opening deeper than to the site where the material is to be dispensed. A further advantage is that the assembly is potentially simpler for these embodiments.

In these embodiments, for the dispensing process, the device is firstly charged with the consumable element. Then the distal end portion of the dispenser element is positioned at a site where dispensing is desired. The advancement force is made to act on the consumable element and the rotation drive is activated to rotate the one element being coupled thereto while the other element is prevented from such rotation. Therewith there is a relative rotation between the distal face of the consumable element and the proximal face of the end portion of the dispenser element, which results in the material with thermoplastic properties at the distal end face of the consumable element to be made flowable and to flow from the liquefaction site to its immediate neighbourhood and which furthermore results in an advancement of the consumable element towards the liquefaction site. Preferably but not necessarily, the dispenser element, or the proximal face of the end portion of the dispenser element respectively, is designed for guiding the flowable material away from the liquefaction site in a predetermined (e.g. axial or radial) dispensing direction. When a desired amount of the flowable material has been dispensed, the rotation is stopped and/or the advancement force is de-activated and the distal device end is removed from the operating site.

In the described removal step, the dispensed material is separated from a part of the same material which was not made flowable and therefore, after the dispensing, remains in the device. If removal of the device from the operating site is effected immediately after or before stopping the rotation (as long as flowable material at or near the liquefaction site is not solid enough yet for forming a strong connection with the dispensed material) such removal can be effected without additional measures. If the distal end of the device is not removed until all material which has been made flowable is re-solidified, it will usually be necessary to shortly re-activate the rotation drive for weakening the connection between the dispensed material and the material at the liquefaction site, i.e. the rest of the consumable element remaining in the device, such that this connection can be broken with little effort and without destroying whatever was to be achieved with the dispensing and re-solidification of the dispensed material.

If, after one dispensing step, a rest of the consumable element remains in the device, a further dispensing step or part thereof can be effected at a different site after simple repositioning of the distal device end and in particular without any need of otherwise handling the device. If, after one or a plurality of dispensing steps, the material with thermoplastic properties present in the device is totally or nearly used up or cannot be made flowable any more for other reasons, the device is recharged by exchanging the consumable element or by adding to a rest of a first consumable element a further consumable element or part thereof.

For a given material to be dispensed, a given liquefaction site geometry, a given rotary power and a given advancement force, the amount of dispensed material is dependent on the time during which the rotation drive and the advancement force are active, or on the travel of the proximal end of the consumable element relative to the dispenser element respectively. The viscosity of the dispensed material flowing from the liquefaction site is primarily dependent on the material itself. But it is further dependent on the friction heat created at the liquefaction site (being dependent on the advancement force and on the relative rotational speed between consumable element and dispenser element) and the amount of flowable material which is made to flow from the liquefaction site by the advancing consumable element, which is again dependent on the advancement force. An increase in the named rotational speed, i.e. in the rpms of the rotation drive, will therefore tend to lower the viscosity of the dispensed material. An increase in the advancement force will tend to raise the viscosity. For automatizing the dispensing process, it therefore may be advantageous to monitor at least one of: the common activity time of rotation drive and advancement force, the travel of the proximal end of the consumable element relative to the dispenser element, rotational speed and energy consumption of the rotation drive, and the size of the advancement force. Therein set parameters are dependent on the material to be dispensed and on the liquefaction site geometry.

The device according to the invention may be a one way device which is used only as long as it contains dispensable material. However, as mentioned already further above, the device according to the invention is preferably not a one way device but is rechargeable. In this, recharging can in accordance with a first option be a recharging with the consumable element only, so that the dispenser element is re-usable. In accordance with a second option, the dispenser element may be intended for on-time use only. For example, the dispenser element may be equipped for remaining anchored, by the material with the thermoplastic properties, in the patient and thereby serve as an implant. As another example of the second option, the dispenser element may be removed after dispensing but then may be in a condition that re-using does not make sense, for example be partially covered by thermoplastic material sticking to it. In this other example, the dispensing element may be disposed of after dispensing.

Recharging of the consumable element only is particularly simple for an embodiment of the device according to the invention, in which the consumable element is cannulated for being arranged around the shaft portion of the dispenser element, in which the dispenser element is coupled to the rotation drive, and in which the consumable element is slotted over its whole length and comprises enough elasticity for being slid in a radial direction over the shaft portion. Other ways for re-charging may include decoupling of the end portion from the shaft portion and/or decoupling of the dispenser element or the consumable element from the rotation drive.

Recharging of the dispensing element and the consumable element may comprise coupling an assembly comprising the dispensing element and the consumable element to the rotation drive or coupling the dispensing element and/or the consumable element individually.

During the dispensing process, the shaft portion of the dispenser element is under a tensile load, and if coupled to the rotation drive needs to be capable of transmitting the torque from this drive to the distal device end. There is no other load put on the shaft portion and therefore the shaft portion of the dispenser element does not necessarily have to be rigid parallel to its longitudinal axis but may be flexible, as long as it is capable of withstanding the tensile load preferably without substantial axial lengthening.

The requirements of device and method according to the invention regarding the consumable element, or the material to be dispensed respectively, are very few. This means that the material can be chosen to best fit the task to be carried out. The material needs to be capable of becoming flowable at a temperature which is preferably not higher than about 350° C. In a solid state and at room or body temperature, the material needs to have mechanical properties to make it capable of transmitting the advancement force, i.e. of standing the corresponding compressive load along its axial length, without being substantially deformed by this force, in particular without substantial enlargement of its cross section. Buckling is not so relevant as it is substantially prevented by the dispenser element. Depending on the embodiment, the consumable element also needs to be capable of transmitting the torque of the rotation drive.

Experiments show that it is possible to dimension the dispenser element and the consumable element of the device according to the invention such that the distal device portion has a diameter of only a few millimeters (e.g. 4 to 8 mm) and an axial length of up to 200 mm or even more. Such dimensions render the device extremely suitable for minimal invasive surgery. Experiments also show that a rotational speeds of between approximately 10,000 and 100,000 rpm are suitable for the above named small diameter consumable elements when made of PLA. This means that rotation drives known from drilling machines as used in surgical operations or such machines themselves may be applicable in the device according to the invention, wherein it may be necessary to increase the rotational speed with the aid of a per se known gear (e.g. planetary gear) or to adapt a coupling means (e.g. chuck) for coupling one of the device elements to the rotation drive.

In all embodiments, optionally in addition to the rotational movement, auxiliary means may be used to help bring the distal (or proximal) face of the consumable element into a flowable state. An example of such an auxiliary means is a heater that for example locally introduces heat into the dispenser element in a vicinity of the proximal or distal face.

The device according to the invention is applicable in substantially all surgical procedures in which a material with thermoplastic properties is a suitable material and is needed in a specific place of an operation site where the material cannot be introduced in a solid state or cannot take over the intended function (e.g. positive fit) if brought in a solid state. Exemplary such surgical procedures are fixation of a suture or wire in a tissue opening, application of spacing material between an endoprosthesis and tissue, introduction of blocking or adhesive material between tissue parts, between tissue and an implanted element or between implanted elements, in-situ forming of anchor pins for fixation of bone plates (e.g. for osteosynthesis), rods (e.g. for spinal fixation), endoprostheses for joint resurfacing, webs or membranes on tissue, augmentation of tissue, in particular of cancellous bone, filling of small tissue defects, repair of endoprosthesis fixation made of bone cement, sealing of cavities as e.g. in tubular bones or dental roots.

A special class of applications of the device according to the invention are applications in which the dispenser element is left where it was positioned for the dispensing process, e.g. in a tissue opening, where it constitutes an implant being anchored in the tissue of bottom and/or walls of the tissue opening. In such embodiments, the dispenser element may comprise an additional functional structure that serves a further purpose. For example, it may comprise one or a combination of:

a securing structure, for example at its proximal end, that serves for a further element to be coupled to the dispenser element (that is an implant) and/or to the tissue in which the dispenser element is anchored;

self-reaming and/or cutting structures that are to create and/or enlarge the tissue opening when the dispenser element is first introduced (Examples of such structures are a self-cutting blade or a tapping thread or the structures taught in WO 2005/079696, incorporated herein by reference. Especially, in the embodiments of WO 2005/079696 that comprise a cannulated solid structure with openings for the thermoplastic material, the taught cannulated solid structure may serve as dispensing element in accordance with the teaching of the present application.);

additional anchoring structures, such as a thread, as for example taught, referring to a pedicle screw in U.S. provisional patent application No. 61/259,383 incorporated herein by reference;

additional functional structures in contact with the tissue, as for example taught in WO 2004/017 857 incorporated herein by reference. Especially, in the embodiments of WO 2004/017 857 that comprise a cannulated solid structure with openings for the thermoplastic material, the taught cannulated solid structure may serve as dispensing element in accordance with the teaching of the present application. An example of additional functional structures are surface regions that are structured to advance osseointegration, for example by having an appropriate coating and/or an appropriate surface roughness. Another example of an additional functional structure is drug delivery structures. Further functional structures of implants, which functional structures are either in contact with the tissue in which the implant is anchored or protrude from this tissue, can be found in U.S. Pat. No. 7,335,205, incorporated herein by reference in its entirety.

A first example of a securing structure is a securing collar or head. For example, if the dispenser element is cannulated (i.e. with an axial opening/cannulation open to the proximal side) with at least one bore through which the thermoplastic material may flow out of the cannulation and into tissue openings and/or other structures, the cannulated portion (cannulated shaft portion) may comprise a proximal outward-extending collar. Such a collar then may be used to secure a further element—such as a plate—against the tissue, when such further element has a through opening with an inner diameter approximately corresponding to the outer diameter of the cannulated portion.

As an alternative or in addition to comprising a collar as the securing structure, other structures also may be present, such as a proximal interior or exterior thread, a post, a feature of a snap-on or bayonet coupling, a rod guiding structure etc.

For example, if the dispenser element is to serve as a dental implant, an interior thread open to the proximal side may serve for securing a basal screw. If the dispenser element is to serve as a dental implant and comprises a post as a securing structure such post may serve for securing a dental crown or dental prosthesis.

As another example, if the dispenser element is to serve as a pedicle screw, it may comprise proximal bolt guiding and/or plate guiding structures for being secured to a spine stabilizing bolt and/or plate or the like.

A cannulated dispenser element serving as an implant element may in many situations be used to replace a classical bone screw with a screw head. Also, when serving as a bone screw replacement, it may, in addition to comprising the mentioned openings, optionally further comprise additional functional structures such as an outer thread, a reaming structure etc.

In addition or as an alternative to replacing a bone screw, the dispenser element may, together with the dispensed material, function in a blind-rivet-like manner. This is if there is no or not enough sufficiently firm tissue at the site where the thermoplastic material is dispensed, anchoring may be achieved by dispensing underneath a layer of firm tissue.

In embodiments, the openings may be positioned to ensure sub-cortical anchoring of the dispenser element. Generally, a sub-cortical anchoring may, for example, be obtained if a distance between an outer surface of the bone tissue and the proximal end of an opening through which the thermoplastic material exits from the cannulation is for example between 2 mm and 7 mm, especially between 3.5 mm and 5.5 mm (this being quantities that hold for grown-up persons). Accordingly, a distance between a distal end face of a further device resting against the bone tissue (such as a fixation device body of a spine stabilization device) and the proximal onset of the opening can be chosen to be of the same order, i.e. between 2 mm and 7 mm, especially between 3.5 mm and 5.5 mm. Also in embodiments for sub-cortical anchoring, the dispenser element may comprise portions that are substantially distally of the opening(s)—in these embodiments, therefore, the end portion may be elongate, and its axial extension may even be comparable to the axial extension of the shaft portion. Examples of outer geometries of dispenser elements may, for example, be found in FIG. 33 or 42 of PCT/CH2010/000045 incorporated herein by reference. Compared to the embodiment of FIG. 43 of PCT/CH2010/000045, the proximal face of the end portion of the element is, for serving as dispenser element according to the present teaching, adapted to allow a relative rotational movement of the consumable element and the dispenser element.

In other applications, the dispenser element is of the kind where the end portion protrudes radially from the shaft portion, with the consumable element, for example, comprising an axial through opening. In embodiments where the dispenser element is to remain anchored in the tissue, the shaft portion may comprise a securing structure, such as a thread and thereafter serve as anchor for a further device, such as a stabilizing device.

A further group of applications concerns augmentation. In such applications, the dispenser element is in most embodiments removed from the tissue after the dispensing process. For example, for augmentation the dispenser element may again be of the cannulated kind. It may be introduced in a tissue opening so that the opening/openings through which the thermoplastic material exits is in vicinity to brittle and/or weak tissue to interpenetrate such tissue. In addition, the dispenser element in such embodiments may serve as a profile body, for example defining the shape of an inner thread of the tissue opening. The function of such a profile body is described for example in U.S. provisional patent application No. 61/259,383 incorporated herein by reference in its entirety. Compared to embodiments of, for example, FIGS. 1-7 of U.S. 61/259,383, the proximal face of the end portion of the element is, for serving as dispenser element according to the present teaching, adapted to allow a relative rotational movement of the consumable element and the dispenser element. The following materials are capable of being dispensed with the aid of the device according to the invention wherein the named materials are, in particular, suitable for dispensing the material in order to establish a load-bearing connection between two tissue parts, between a tissue part and an implanted item or between two implanted items:

resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymethacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylenesulfides, polysulfones, polyethers or equivalent copolymers or composite materials containing the named polymers as a component. Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Non-resorbable materials such as polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec). A further suitable group of polymers are Polycarbonate Urethanes, such as, for example the products sold under the trade name "Bionate®" by DSM Biomedical, especially products with a hardness of between 55 shore D and 75 shore D, especially the hardness grades 55D, 65D, and 75D.

The materials to be dispensed may contain foreign phases or compounds serving further functions. In particular, a thermoplastic base material may be strengthened by admixed fibers or whiskers (e.g. of calcium phosphate ceramics or glasses) and such represent a composite material. The thermoplastic material may further contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel).

Osseo-integration stimulating fillers that are only partially or hardly degradable, for non degradable polymers include: Bioglasses, Hydroxyapatite (>90% cristyllinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20.

Embodiments of bioactive fillers and their discussion can for example be found in X. Huang and X. Miao, J Biomater App. 2007 April; 21(4):351-74), J A Juhasz et al. Biomaterials, 2004 March; 25(6):949-55.

Particulate filler types include: coarse type: 5-20 μm (contents, preferentially 10-25% by volume), sub-micron (nanofillers as from precipitation, preferentially plate like aspect ratio>10, 10-50 nm, contents 0.5 to 5% by volume).

BRIEF DESCRIPTION OF THE DRAWINGS

A few exemplary embodiments of the device according to the invention are described in detail in connection with the following Figs., wherein.

DETAILED DESCRIPTION OF THE INVENTION

Figure 1:
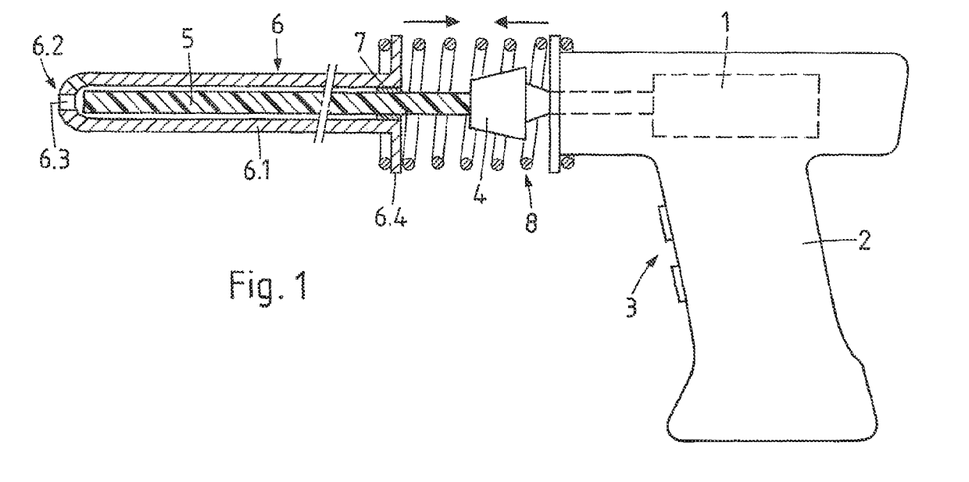
FIG. 1 is a longitudinal section through a first exemplary embodiment of the device according to the invention in which the consumable element is coupled to the rotation drive and is arranged in an axial through opening of the dispenser element.

FIG. 1 is an axial section through a first exemplary embodiment of the device according to the invention. The device comprises a rotation drive 1 located in a housing 2, wherein the housing is designed e.g. for being hand held by an operator and comprises control buttons 3 e.g. for power on/off, for controlling or setting the rotational speed and/or the power consumption. A chuck 4 is connected to the rotation drive and serves for coupling the consumable element 5 to the rotation drive 1. Instead of the chuck 4 any other coupling means such as e.g. a screwed connection is applicable for coupling the consumable element to the rotation drive. The consumable element 5 is a stiff rod of which at least a distal portion consists of the material to be dispensed. The dispenser element 6 comprises a cannulated shaft portion 6.1 and a distal end portion 6.2 which closes the cannulated shaft portion partly. The axial length of the dispenser element 6 is smaller than the axial length of the consumable element 5.

The distal end portion 6.2 of the dispenser element closes the cannulated shaft portion only partly, i.e. it comprises openings 6.3 e.g. bores extending in an axial to radial direction or it consist of or comprises a material comprising an open porosity (e.g. sintered metal or ceramic material or metal foam) and being suitable for transfer of the flowable material from the inside of the dispenser element to the surroundings thereof. The end portion 6.2 may be arranged on the shaft portion 6.1 to be removable (e.g. threaded or snapped on) or not removable (e.g. integral part of shaft portion or welded thereto). The through opening of the shaft portion 6.1 is dimensioned such that rotation of the consumable element 4 causes no, or only very little, lateral friction. For keeping the consumable element and the shaft portion in coaxial alignment, a bearing 7 (preferably bush bearing) may be arranged in a proximal region of the dispenser element.

For a dispensing process, the consumable element 5 is coupled to the rotation drive, introduced in the dispenser element 6 with its distal face facing the proximal face of the end portion 6.2 of the dispenser element 6. For a fully manual dispensing process, it is an operator who holds the housing 2, forces it in a direction towards the dispenser element 6 (advancement force) and activates the rotation drive. At the same time he holds the dispenser element 6 by its proximal end for counteracting the advancement force and for preventing the dispenser element 6 from rotating. For this holding the dispenser element 6 may comprise a proximal flange 6.4 or other radial protrusion. Part of the named functions of the operator may be taken over by a tissue surface against which the flange 6.4 of the end portion 6.2 is pressed by the advancement force. When the rotation drive 1 and the advancement force are active, the distal face of the consumable element 5 is rotated relative to the end portion 6.2 of the dispenser element 6 such causing friction and heating of the material with thermoplastic properties which thereby is made flowable, and by the advancement force is driven through the openings 6.3 of the end portion 6.2 of the dispenser element 6 to be dispensed at a site on the outside thereof.

The above described operator actions regarding holding the dispenser element 6 and pressing the housing 1 against it can also be achieved with a resilient element 8 (e.g. spring) which is mounted between the proximal end of the dispenser element 6 (e.g. flange 6.4) and the housing 2 such that it pulls these towards each other. It may be possible also that the resilient element 8 functions as a centering element in addition to bearing 7 or in the place of it.

The openings 6.3 of the end portion of the dispenser element can be adapted to guide the flowable material in a specific direction. This direction may be e.g. an axial direction, a plurality of radial directions regularly spread around the circumference of the dispenser element 6, one specific radial direction, a plurality of specific radial directions, or a direction or directions which are combinations of the named directions.

The dispenser element 6 being a part of the device according to the invention is in some embodiments removed together with the rest of the consumable element 5 and the rotation drive 1 in housing 2. In particular, in the case of the operator handling the device which does not comprise the resilient element 8 (dispenser element 6 possibly not connected to any of the other device parts) or in which the connection between a resilient element and the dispenser element is releasable, the dispenser element 6 may easily be left where it was positioned for the dispensing process, e.g. in a tissue opening, where it constitutes an implant being anchored in the tissue of bottom and/or walls of the tissue opening. In this case, the dispenser element may be part of a larger implant and therefore have a form which is dictated by the implant function.

As can be seen from FIG. 1 the geometry of the chuck 4 in relation to the proximal end of the dispenser element limits the possible advancement of the consumable element 5 in the dispenser element. For this reason it is possible to arrange the material with the thermoplastic properties in a distal portion of the consumable element 5 only and give this distal portion an axial length which corresponds at least with the possible travel of the proximal end of the consumable element 5.

In particular, if the material to be dispensed becomes flowable only in a relatively high temperature range, it may be advantageous to make the dispenser element 6 of a heat insulating material (e.g. thermoset polymer or ceramic material) such that the thermal load put on the tissue at the site of dispensing is reduced to only the heat energy of the flowable material.

As, in the first embodiment of the device according to the invention, the rotating consumable element 5 is sheltered from contact with tissue by the dispenser element 6 and therefore cannot damage tissue, this embodiment is particularly suitable for dispensing processes at the bottom of narrow tissue openings in which contact between the distal device portion and the tissue, other than where dispensing is desired, can hardly be fully prevented.

For recharging the device according to FIG. 1 the dispenser element 6 may be removed from the device, the consumable element 5 de-coupled from the rotation drive 1, a new consumable element 5 coupled to the rotation drive 1 and the dispenser element 6 again mounted on the new consumable element 5. Instead of removing and re-mounting the whole dispenser element 6, it is possible also to only remove and re-mount the end portion 6.2 of the dispenser element 6. It is possible also to add or replace a distal portion of the consumable element 5 by attaching it to a proximal portion thereof. Such attachment may be effected by e.g. screwing a distal portion of the dispensable material to a proximal portion which is not made of the dispensable material or by welding a further distal portion to a partly used distal portion of the dispensable material, wherein in any case care must be taken, that the connection between portions of the consumable element 5 are capable of transmitting the torque created by the rotation drive 1. Very easy recharging is possible if a cannulated drilling machine (as used e.g. in surgery in connection with a K-wire) constitutes the rotation drive, wherein for recharging the chuck is deactivated, a new consumable element is pushed through the rotation drive and the chuck is reactivated for clamping a proximal end of the new consumable element.

In embodiments where sheltering of tissue from rotational movement is not a requirement, the embodiment of FIG. 1 could be modified so that the dispenser element 6 is subject to rotational movement while the consumable element 5 is held still.

FIGS. 2A to 2G illustrate further embodiments of distal device ends (axial sections and cross sections through dispenser element 6 and consumable element 5) which are applicable in the device according to FIG. 1.

Figure 2A:
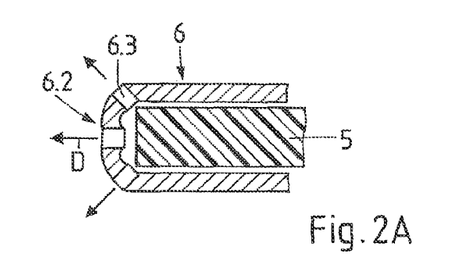
FIGS. 2A to 2G show in a larger scale further exemplary embodiments of distal device portions (axial sections and cross sections through consumable element and dispenser element) applicable in the device according to FIG. 1.
Figure 2B:
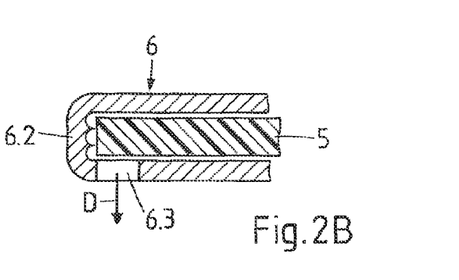

FIGS. 2A and 2B show end portions 6.2 of the dispenser element 6 with differently oriented openings 6.3 for guidance of the flowable material to be dispensed in different directions D as already mentioned further above. Therein size and form of the openings are freely selectable within a wide range.

Figure 2C:
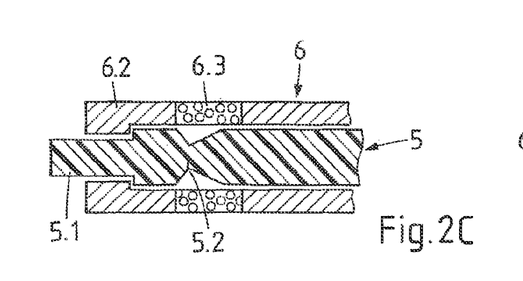

FIG. 2C illustrates a distal device end in which a distal appendix 5.1 of the consumable element 5 is made to function as part of the end portion 6.2 of the dispenser element 6. The appendix 5.1 comprises in a distal region a non-round cross section being smaller than the cross section of the consumable element 5 and is connected to the distal end of the consumable element 5 via a predetermined braking point 5.2. The advancement force pushes the appendix 5.1 into a distal portion of the dispenser element 6 which comprises an axial channel with a corresponding non-round cross section, therewith preventing rotation of the appendix 5.1 when the rotation drive is activated such that the predetermined breaking point 5.2 is broken and the material to be dispensed is made flowable at the site of the broken predetermined breaking point.

Figure 2D:
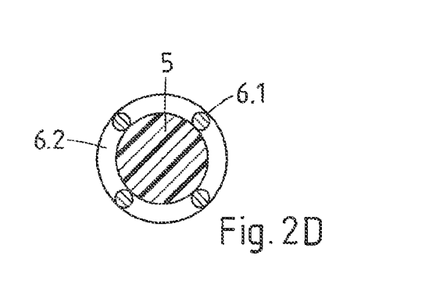
Figure 2E:
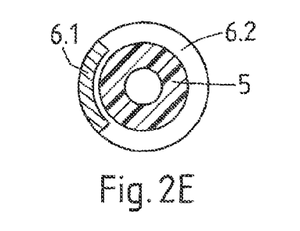

FIGS. 2D and 2E are cross sections through the shaft portion 6.1 of the dispenser element and the consumable element 5 viewed against the proximal face of the end portion 6.2 of the dispenser element 6. In contrast to the embodiments according to FIG. 1 and FIGS. 2A to 2C, the shaft portion 6.1 has not the form of a cannulated tube, but is constituted according to FIG. 2D by a plurality of longish rods distributed in a regular or irregular pattern around the circumference of the consumable element 5 to form a cage, wherein a solid or perforated bottom plate forms the end portion 6.2 of the dispenser element 6. FIG. 2E shows a shaft portion 6.1 consisting of only one longish rod (possibly having the form of a part of a hollow cylinder) and an end portion 6.2 extending non coaxially therefrom. FIG. 2E further shows a cannulated consumable element having the advantage of a greater mechanical stiffness than a corresponding non-cannulated element comprising the same cross sectional area, and not comprising a central portion which due to none or only little rotational speed may be difficult to be brought into a flowable state.

Figure 2F:
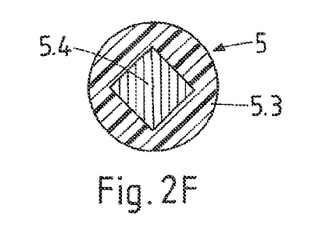
Figure 2G:
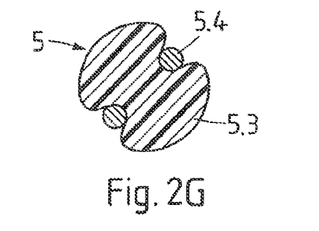

FIGS. 2F and 2G are cross sections through the consumable element 5 where a distal portion 5.3 of the consumable element 5 made of the dispensable material and a proximal portion 5.4 not made of the dispensable material are connected to each other. The connection is a press fit or push fit in axial direction and designed for preventing rotation of the portion relative to each other. According to FIG. 2F the proximal portion 5.4 has a non-round cross section (e.g. square) and the distal portion 5.3 has a corresponding blind hole or axial channel. According to FIG. 2G the proximal portion 5.4 has a plurality of distal protrusions which fit into axial grooves on the circumference of the distal portion 5.3.

The first embodiment of the device according to the invention as shown in FIG. 1 may be further varied as proposed in the following paragraphs without departing from the scope of the invention:

The resilient element 8 is mounted between the proximal end of the dispenser element 6 and the rotation drive 1 or a proximal portion of the consumable element 5.

The shaft portion 6.1 and/or the end portion 6.2 of the dispenser element 6 is at least partly not rigid but flexible (wire, rope, membrane, web, non-woven etc.).

The rotation drive comprises an angular gear or bevel gear to enable the distal device portion to be angled relative to the rotation axis of the rotation drive.

Instead of the consumable element 5, the dispenser element 6 is coupled to the rotation drive 1 (e.g. cannulated drilling machine) and the consumable element 5 is held to prevent it from rotating.

Figure 3:
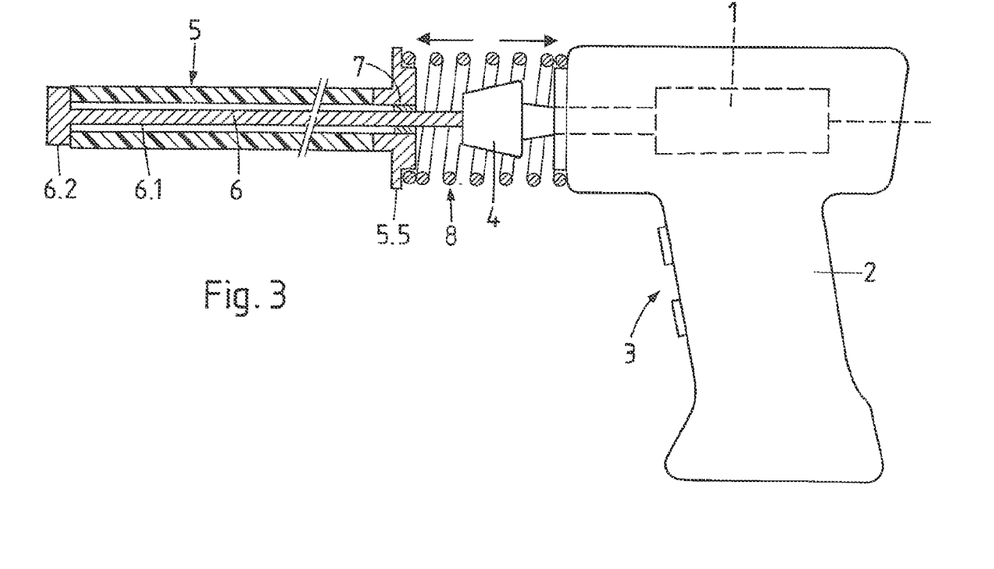
FIG. 3 is a longitudinal section through a second embodiment of the device according to the invention in which the dispenser element is coupled to the rotation drive and the consumable element is cannulated and arranged around the shaft portion of the dispenser element.

FIG. 3 illustrates a second embodiment of the device according to the invention. The device of FIG. 3 differs from the device of FIG. 1 in that the shaft portion 6.1 of the dispenser element 6 extends through an axial through opening of the consumable element 5, the proximal end of the shaft portion 6.1 being coupled to the rotation drive 1 and the distal end portion 6.2 extending radially, e.g. coaxially, from the shaft portion 6.2 such that it cannot enter the through opening of the consumable element 5. The axial length of the shaft portion 6.1 is greater than the axial length of the consumable element 5.

The elements of the device according to FIG. 3 correspond in part of their functions with the elements of the device according to FIG. 1 wherein another part of the functions is exchanged. Similar elements are all the same denominated with same referenced numerals and are described in the following paragraphs only where they cannot be deduced from the description of FIG. 1 in an obvious manner.

The material of the distal end of the consumable element 5, which is the material with thermoplastic properties and is to be dispensed, is made flowable through friction heat created between the proximal face of the end portion 6.2 of the dispenser element 6 and the distal face of the consumable element 5 by rotation of the dispenser element 6. For effecting the friction and the advancement of the proximal end of the consumable element 5, an operator holds e.g. the housing 2 and pushes the proximal end of the consumable element 5 against the end portion 6.2, for which purpose the proximal end of the consumable element 5 may comprise a flange 5.5 or other radial protrusion. The same is achieved by mounting a resilient element 8 between the proximal end of the consumable element 5 and the housing 2, the rotation drive 1, or a proximal portion of the shaft portion 6.1, wherein the resilient element 8 is biased to push the named elements away from each other such forming a load frame in which the consumable element 5 is put under a compressive load and the shaft portion 6.1 of the dispenser element 6 is put under a tensile load.

Again a proximal portion of the consumable element 5 may not consist of the material to be dispensed wherein there is no need for the different portions of the consumable element 5 to be connected with each other.

For re-charging the device according to FIG. 3, the end portion 6.2 of the dispenser element 6 is removed or the dispenser element 6 is de-coupled from the rotation drive 1, a new or additional distal portion of the consumable element 5 or a new consumable element 5 (one or a plurality of pieces) is mounted on the shaft portion 6.1 in an axial direction, wherein there is no necessity for new portions to be connected with old portions or new pieces to be connected between each other. Alternatively, the portion of the consumable element 5 to be added or exchanged is slotted over its entire axial length and is mounted on the shaft portion while, if applicable, the resilient element 8 is sufficiently compressed to make room for the new portion. In the latter case there is no need to remove or de-couple any other element of the device. The same applies if the consumable element has the form of an elastically deformable spiral which is "screwed" onto the shaft portion. As yet another alternative, the entire dispenser element may be exchanged for recharging, together with exchanging the consumable element.

Figure 4A:
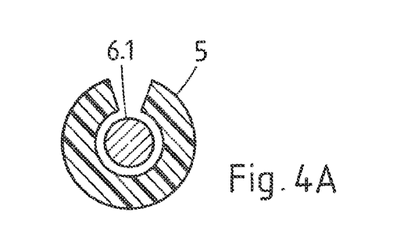
FIGS. 4A to 4C show in a larger scale further exemplary embodiments of distal device portions (axial sections and cross sections through the dispenser element and the consumable element) applicable in the device according to FIG. 3.
Figure 4B:
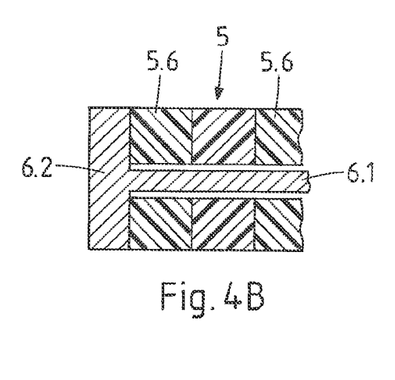
Figure 4C:
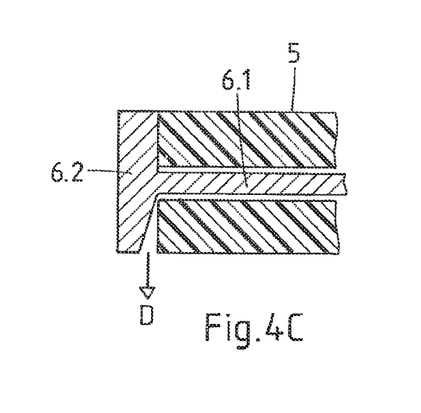

FIGS. 4A to 4C are cross sections and axial sections through the distal device portion, i.e. through the consumable element 5 and the dispenser element 6. FIG. 4A illustrates (cross section) a consumable element 5 (or distal portion thereof) which is suitable for the above described axial recharging. The condition for such radial re-charging is a sufficient elasticity of the material to be dispensed for the shaft portion 6.1 being able to be slid into the consumable element 5 or portions thereof. FIG. 4B (axial section) illustrates a distal portion of the consumable element 5 consisting of a plurality of bead-like items 5.6 which are not connected to each other. FIG. 4C (axial section) illustrates means for guiding the flowable material in a predetermined direction D away from the end portion 6.2 of the dispenser element 6. For this purpose the proximal face of the end portion 6.2 comprises at least one radial channel oriented in the direction D and possibly sloping towards the circumference of the end portion.

The device according to FIG. 3 may be altered as described in the following paragraphs without departing from the scope of the invention:

The resilient element 8 is mounted between the proximal end of the consumable element 5 and the rotation drive 1 or a proximal portion of the dispenser element 6.

A proximal end of the shaft portion 6.1 of the dispenser element 6 is a flexible rod or rope guided in a flexible cannula and allowing a freely selectable angle between the rotation axis of the rotation drive 1 and the longitudinal axis of the consumable element 5.

The consumable element is coupled to the rotation drive (e.g. cannulated drilling machine) and the dispenser element is held for counteracting the advancement force and for preventing the consumable element from rotating with the dispenser element.

Figure 7:
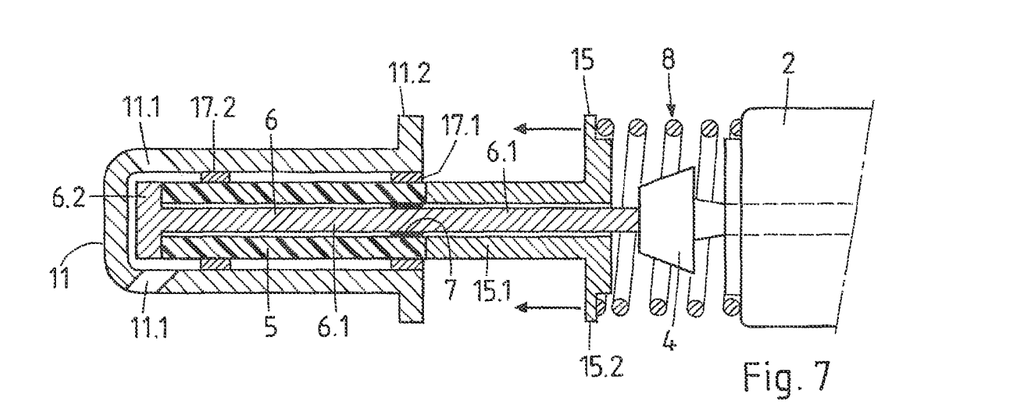
FIG. 7 shows a further embodiment of the device according to the invention.

Yet a further variant of the device according to FIG. 3 is illustrated in FIG. 7. As in the embodiment of FIG. 3, the dispenser element 6 is coupled to the rotation drive (of which only a proximal end portion of the housing 2 is illustrated in FIG. 7), and the shaft portion 6.1 of the dispenser element extends through an axial through opening of the consumable element 5. In the embodiment of FIG. 7, however, the tissue is shielded from the rotational movement by an additional protective sheath 11. The protective sheath has an elongate cavity that extends in the proximodistal direction and is open to the proximal side for introduction of the dispenser-element-consumable-element assembly. The protective sheath further has at least one opening 11.1 through which the liquefied thermoplastic material can exit and be pressed into structures of the tissue.

In many embodiments, the interface between the end portion 6.2 of the dispenser element 6 and the consumable element 5 will be held at a constant position in vicinity of the opening 11.1. Therefore, in these embodiments, the consumable element will be subject to a forward movement (a movement into the distal direction) when being consumed. To this end, in accordance with a first option the consumable element will be designed to protrude substantially from the proximal end face of the protective sheath 11 so that it can be pushed further into the sheath during the dispensing process. In accordance with a second option, the device further comprises a pusher 15 adapted to engage into the elongate cavity and to push the consumable element further to the distal side when it gets shorter while being consumed. In the depicted configuration, the pusher 15 comprises a shaft portion 15.1 with an outer diameter adapted to the inner diameter of the elongate cavity. The resilient element 8—if present—may then be arranged between the housing 2 and a flange 15.2 of the pusher to push the same to the distal direction. An outer support not depicted in FIG. 7 may in addition connect the protective sheath 11—for example a collar portion 11.2 thereof—to the housing 2 to fix the relative position, possibly in a manner that it encloses and shields the resilient element and the pusher. The pusher may be coupled, for example attached, to the consumable element to prevent a rotational movement thereof.

An additional bearing or additional bearings 17.1, 17.2 may be present between the protective sheath 11 and the consumable element 5 to guide the latter in the elongate cavity; since the consumable element 5 is not to rotate the bearings optionally by rotationally asymmetric and engage into structures (such as longitudinal trenches) of the consumable element to prevent their rotational movement. In addition or as an alternative, the elongate cavity may be rotationally asymmetric with the consumable element outer shape adapted thereto, the consumable element being slidingly inserted.

In the embodiment of FIG. 7, for example the protective sheath may remain in the tissue opening after the dispensing process to serve as implant or implant part therein after the process. Alternatively, it is also possible that the protective sheath is removed after the process.

Of course, also in the embodiment of FIG. 7, the arrangement may be changed in that the consumable element 5 is caused to rotate while the dispenser element 6 is held still.

Figure 5:
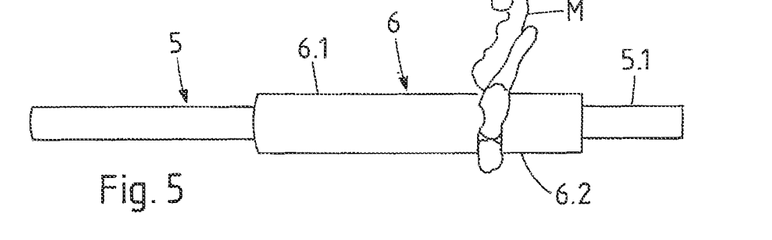
FIG. 5 is a photograph of a distal device end according to FIG. 2C from which flowable material has been dispensed.

FIG. 5 illustrates a dispensing process in which PLA is dispensed from the distal end of the device according to FIG. 1 which is equipped as shown in FIG. 2C. Same elements are denominated with same reference numerals as in the preceding Figs. The illustrated dispensing process was carried out with a Dremel hand grinding machine (30,000 rpm) to which the consumable element 5 was coupled. The consumable element 5 consisted of PLA and had a length of 80 mm and a diameter of 3 mm (predetermined breaking point diameter 2 mm) and a length of 80 mm. The dispenser element had an outer diameter of 5 mm and an inner diameter of 3.1 mm and four bores for discharge of the liquefied material were arranged regularly around the circumference of the dispenser element and had a diameter of 1.6 mm. FIG. 5 clearly shows the dispensed material M in a re-solidified state after a dispensing process of about 1 to 4 s and using an advancement force of between about 3 to 10N, in which dispensing process the consumable element was advanced by about 10 mm.

Figure 6:
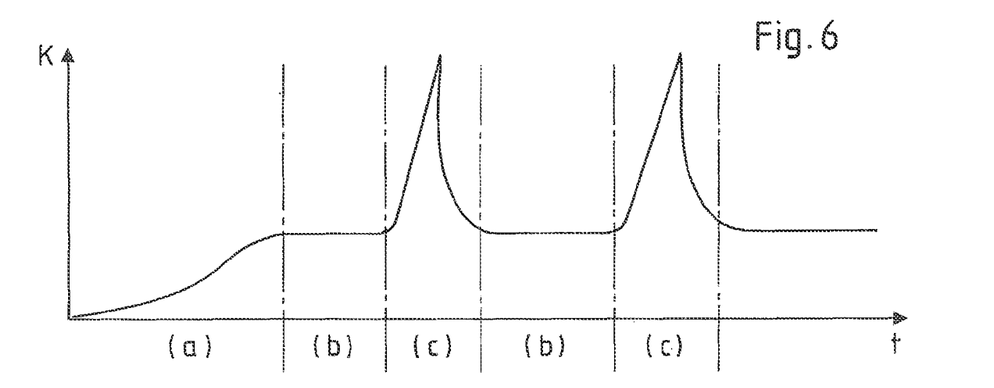
FIG. 6 illustrates an exemplary control sequence of a dispensing process.

FIG. 6 is a diagram (advancement force K vs. time t) representing an exemplary control sequence for a dispensing process with the aid of a device according to the invention. The sequence starts with a start-up phase (a) in which the rotation is switched on and the advancement force is built up. The start-up phase is followed by alternating melting phases (b) and discharge phases (c), wherein the advancement force has a medium strength in the melting phases and is briefly increased during the discharge phases.

In addition to the friction heat created by the relative rotation between consumable element and dispenser element, it is possible to apply further heating energy to the consumable element in the area of its distal face for furthering the liquefaction process. Such further heating energy may be constituted by resistively or inductively heating the end portion of the dispenser element or in particular by adsorbing electromagnetic radiation, e.g. laser light in this end portion, wherein the laser light is preferably coupled into the proximal end of the consumable element and is guided through the consumable element to be absorbed in the end portion of the dispenser element.

Figure 8:
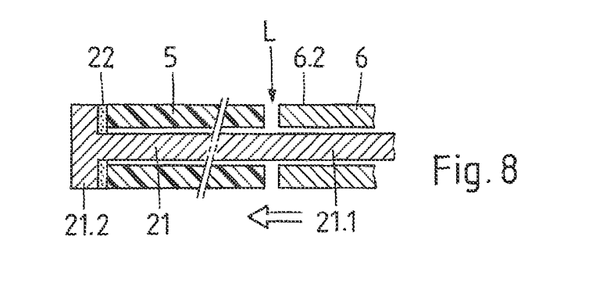
FIG. 8 illustrates a variant with a liquefaction site that is proximal of the consumable element.

FIG. 8 yet schematically illustrates a variant in which the liquefaction site L is proximally of the consumable element. A counter element 21 is used to apply the counter force to the assembly and to either hold the consumable element 5 for not rotating or to transmit the rotation to the consumable element. The counter element 21 comprises a counter element shaft portion 21.1 and a counter element distal end portion 21.2 with a larger cross sectional area than the shaft portion, so that the distal end portion comprises a proximal face for coupling the counter force and the necessary angular momentum (for holding the consumable element to not rotate or for causing it to rotate) into the consumable element. The consumable element 5 is fastened to the counter element 21, for example by an adhesive 22. The relative rotational movement of the dispenser element 6 and the counter element 5 acts at the liquefaction site L.

The concept of the variant of FIG. 8 may readily be adapted to embodiments additionally comprising an outer protective sheath or to embodiments in which the counter element has the shape of an outer sheath encompassing the consumable element, the outer sheath having at least one opening and preferably a plurality of openings at different axial positions through which the liquefied material can exit into the tissue.

The invention claimed is:

1. A device for dispensing a material with thermoplastic properties in a flowable state at an operation site in a human or animal patient, the device comprising:
    a rotation drive,
    a dispenser element comprising a shaft portion with a longitudinal axis extending from a proximal end of the shaft portion to a distal end portion which is arranged at a distal end of the shaft portion and comprises a proximal or distal face, and
    a consumable element with a longitudinal axis extending from a proximal end to a distal end, at least a portion of the consumable element consisting of the material with thermoplastic properties,
    wherein either the consumable element or the shaft portion is adapted to the rotation drive to be coupled thereto and the consumable element or the shaft portion is designed to be capable of transmitting the torque of the rotation drive to its distal end, and the other one of the consumable or dispenser element is adapted to be held so as to not rotate,
    wherein the consumable element and the dispenser element are arranged or arrangeable with their longitudinal axes parallel to each other, and with a distal or proximal face of the consumable element in contact with the proximal or distal face of the end portion and the two faces are capable of being pressed against each other with an advancement force putting a compressive load on the consumable element along its longitudinal axis and being applied to the proximal end of the consumable element and a counter force to the distal end of the consumable element,
    whereby a relative rotational movement and therewith frictional energy between the consumable element and the dispenser is creatable, which friction energy causes the material with thermoplastic properties to be transformed from the solid into the flowable state.

2. The device according to claim 1, wherein the face of the distal end portion is the proximal face facing towards the proximal end of the shaft portion, wherein at least a distal portion of the consumable element consists of the material with thermoplastic properties, wherein either the proximal end of the consumable element or the shaft portion is adapted to the rotation drive to be coupled thereto and the consumable element or the shaft portion is designed to be capable of transmitting the torque of the rotation drive to its distal end, and the proximal end of the other one of the consumable or dispenser element is adapted to be held so as to not rotate, wherein the consumable element and the dispenser element are arranged or arrangeable with their longitudinal axes parallel to each other, and with the distal face of the consumable element in contact with the proximal face, and wherein the counter force is applicable to the distal end of the consumable element by being applied to the proximal end of the shaft portion, the counter force putting a tensile load on the shaft portion along its longitudinal axis.

3. The device according to claim 1, further comprising a resilient element arranged to form a load frame in which the advancement force and the counterforce are active.

4. The device according to claim 1, wherein the shaft portion of the dispenser element comprises an axial through opening, wherein the end portion partly closes the through opening, and wherein the consumable element is dimensioned for being placed into the through opening of the shaft portion with its proximal end protruding from the proximal end of the shaft portion.

5. The device according to claim 4, wherein the proximal end of the consumable element is coupled or couplable to the rotation drive.

6. The device according to claim 5, wherein for applying the counter force, the proximal end of the shaft portion is equipped with a radial protrusion.

7. The device according to claim 4, wherein a coupling between the rotation drive and the shaft portion and/or a connection between the shaft portion and the end portion is reversible.

8. The device according to claim 1, wherein the end portion protrudes radially from the shaft portion, wherein the consumable element comprises an axial through opening and is dimensioned for being arranged or arrangeable with the shaft portion extending through the through opening of the consumable element, the end portion protruding at a distal end of the consumable element and the proximal end of the shaft portion protruding at the proximal end of the consumable element.

9. The device according to claim 8, wherein a proximal end of the shaft portion of the dispenser element is coupled or couplable to the rotation drive.

10. The device according to claim 9, wherein the proximal end of the consumable element is equipped with a radial protrusion.

11. The device according to claim 8, wherein a coupling between the rotation drive and the shaft portion and/or a connection between the shaft portion and the end portion are reversible.

12. The device according to claim 8, wherein the consumable element or a separate portion thereof comprises a slot extending over its full length, the slot and a corresponding elasticity allowing the consumable element or portion thereof to be put on the shaft portion in a radial direction.

13. A method for dispensing a material with thermoplastic properties in a flowable state at an operating site in a human or animal patient, the method comprising the steps of:
providing a device according to claim 1 in which device the consumable element is arranged on or in the shaft portion and the shaft portion or the consumable element is coupled to the rotation drive, wherein the face of the distal end portion is a proximal face facing towards a proximal end of the shaft portion, wherein at least a distal portion of the consumable element consists of the material with thermoplastic properties, wherein either a proximal end of the consumable element or the shaft portion is adapted to the rotation drive to be coupled thereto and the consumable element or the shaft portion is designed to be capable of transmitting the torque of the rotation drive to its distal end, and a proximal end of the other one of the consumable or dispenser element is adapted to be held so as to not rotate, wherein the consumable element and the dispenser element are arranged or arrangeable with their longitudinal axes parallel to each other, and with a distal face of the consumable element in contact with the proximal face, and wherein the counter force is applicable to the distal end of the consumable element by being applied to the proximal end of the shaft portion, the counter force putting a tensile load on the shaft portion along its longitudinal axis,
positioning the distal end portion at the site where dispensing is desired,
applying the advancement force and the counter force and activating the rotation drive for a time sufficient for bringing material at the distal face of the consumable element into a flowable state,
whereby a relative rotational movement and therewith friction energy between the consumable element and the dispenser element is created, which friction energy causes the material with thermoplastic properties to be transformed from the solid into the flowable state,
and driving away from the end portion towards the site where dispensing is desired,
de-activating the rotation drive,
removing the distal device end from the site where dispensing is desired, thereby separating, if applicable, a dispensed portion of the material with thermoplastic properties from a rest portion of the material with thermoplastic properties which rest portion is removed with the device.

14. The method according to claim 13, wherein after the step of removing, the device is re-charged with a new or additional consumable element or portion thereof.

15. The method according to claim 14, wherein in the step of re-charging, the consumable element or portion thereof is introduced into the device in an axial or a radial direction.

* * * * *